(12) United States Patent
Cuny et al.

(10) Patent No.: US 6,486,324 B2
(45) Date of Patent: Nov. 26, 2002

(54) RING OPENING METATHESIS OF ALKENES

(75) Inventors: Gregory D. Cuny, Hudson; Jingrong Cao, Shrewsbury; James R. Hauske, Hopkinton, all of MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/767,376

(22) Filed: Jan. 23, 2001

(65) Prior Publication Data

US 2002/0042406 A1 Apr. 11, 2002

Related U.S. Application Data

(62) Division of application No. 08/818,197, filed on Mar. 14, 1997, now Pat. No. 6,177,464.

(51) Int. Cl.$^7$ .......................................... C07D 221/04
(52) U.S. Cl. .................................... 546/183; 546/112
(58) Field of Search .............................. 546/141, 150, 546/112, 183

(56) References Cited

U.S. PATENT DOCUMENTS

| | | | |
|---|---|---|---|
| 4,945,144 A | 7/1990 | Grubbs et al. | 426/268 |
| 5,342,909 A | 8/1994 | Grubbs et al. | 526/171 |
| 5,510,240 A | 4/1996 | Lam et al. | 435/7.1 |

OTHER PUBLICATIONS

Sato, Heterocycles 28 (1) 117–120 1989.*
Balkenhohl, F. et al., "Combinatorial Synthesis of Small Organic Molecules", *Angew. Chem. Int. Ed. Engl.*, 35:2288–2337 (1996).
Cuny, G.D. et al. "Ring Opening Cross–Metathesis on Solid Support" *Tetrahedron Lett.* vol. 38 No. 30 (1997) 5237–5240.
Zuercher, W. et al., "Tandem Ring Opening—Ring Closing Metathesis of Cyclic Olefins," *J. Am. Chem. Soc.*, vol. 118, 6634–40 (1996).
Hauske, J. et al., "A Solid Phase CBZ Chloride Equivalent—A New Matrix Specific Linker", *Tetrahedron Letters*, vol. 36, No. 10, pp. 1589–1592 (1995).
Randall, M. et al., "Selective Ring–Opening Cross–Metathesis. Short Metathesis of Multifidene and Viridene", *J. Am. Chem.*, vol. 117, pp. 9610–9611 (1995).
Schneider, M. et al., "Synthesis of Highly Substituted Cyclo–pentane and Tetrahydrofuran Derivatives by Crossed Olefin Metathesis", *Angew. Chem. Intl. Ed. Engl.*, vol. 35, No. 4, pp. 411–412 (1996).
Schneider, M. et al., "Selective Ring–Opening Olefin Metathesis of Functionalized Monosubstituted Olefins", *Angew. Chem. Int. Ed. Engl.*, vol. 36, No. 3, pp. 257–259 (1997).
Snapper, M. et al. "Regio– and Stereoselective Ring–Opening Cross–Metathesis. Rapid Entry into Functionalized Bicyclo[6.3.0] Ring Systems", *J. Am. Chem. Soc.*, vol. 119, pp. 1478–1479 (1997).

Grubbs, R. et al., "Ring–Closing Metathesis and Related Processes in Organic Synthesis," *Acc. Chem. Res.*, vol. 28, 446–52 (1995).
Houri, A. et al., "Cascade Catalysis in Synthesis. An Enantioselective Route to Sch 38516 (and Fluvirucin B1) Aglycon Macrolactam," *J. Am. Chem. Soc.*, vol. 117, 2943–2944 (1995).
Kim, S. et al., "Catalytic Ring Closing Metathesis of Dienynes: Construction of Fused Bicyclic [n.m.0] Rings," *J. Org. Chem.*, vol. 61, 1073–81 (1996).
Kim, S. et al., "Catalytic Ring Closing Metathesis of Dienynes: Construction of Fused Bicyclic Rings," *Journal of the American Chemical Society*, vol. 116, No. 23, 10801–2 (1994).
Martin, S. and Wagman, A., "A Novel Approach to FR–900482 Via Ring Forming Metathesis," *Tetrahedron Letters*, vol. 36, No. 8, 1169–70 (1995).
Martin, S. et al., "A Novel Approach to the Asymmetric Synthesis of Manzamine A. Construction of the Tetracyclic ABCE Ring System," *Tetrahedron Letters*, vol. 35, No. 5, 691–4 (1994).
Martin, S. et al., "Novel Route to Fused Nitrogen Heterocycles by Olefin Metathesis," *Tetrahedron Letters*, vol. 35, No. 33, 6005–8 (1994).
Miller, S. and Grubbs, R., "Synthesis of Conformationally Restricted Amino Acids and Peptides Employing Olefin Metathesis," *J. Am. Chem. Soc.*, vol. 117, 5855–6 (1995).
Miller, S. et al., "Catalytic Ring–Closing Metathesis of Dienes: Application to the Synthesis of Eight–Membered Rings," *J. Am. Chem. Soc.*, vol. 117, 2108–9 (1995).
Noels, A. et al., "Competitive Cyclopropanation and Cross–metathesis Reactions of Alkenes Catalysed by Diruthenium Tetrakis Carboxylates," *J. Chem. Soc. Chem. Commun.*, 783–4 (1988).
Schmalz, H., "Catalytic Ring–Closing Metathesis: A New, Powerful Technique for Carbon–Carbon Coupling in Organic Synthesis," *Angew. Chem. Int. Ed. Engl.*, vol. 34, No. 17, 1833–6 (1995).
Schuster, M. et al., "Ruthenium–Catalyzed Metathesis of Polymer–Bound Olefins," *Angew. Chem. Int. Ed. Engl.*, vol. 35, No. 17, (1996).
Schwab, P. et al., "A Series of Well–Defined Metathesis Catalysts Synthesis of [RuCl2 (=CHR')(PR3)2] and its Reactions," *Angew. Chem. Int. Ed. Engl.*, vol. 34, No. 18, 2039–2041 (1995).
Schwab, P. et al., "Synthesis and Applications of RuCl2 (=CHR')(PR3)2: The Influence of the Alkylidene Moiety on Metathesis Activity," *J. Am. Chem. Soc.*, vol. 118, 100–110 (1996).

(List continued on next page.)

*Primary Examiner*—Robert Gerstl
(74) *Attorney, Agent, or Firm*—Dana M. Gordon; Foley Hoag LLP

(57) ABSTRACT

Methods for performing ring-opening cross-metathesis reactions on solid support are disclosed. Substituted cyclic compounds, libraries of the compounds, and methods of using the compounds to treat bacterial infections are also disclosed.

5 Claims, No Drawings

OTHER PUBLICATIONS

Sigova, V.I. and Konshin, M.E., "Cyclization of 6–Phenyl–2–Styrylnicotinamide into Substituted 7,8–Dihydro–1,6–Naphthyridin–5 (6H)–Ones," *Zhurnal Obshchei Khimii*, vol. 54, No. 9, 2083–5 (1984).

Sigova, V.I. and Konshin, M.E., "Investigation of Naphthyridines: Synthesis of Substituted 5–OXO–5,6,7,8–Tetrahydro–1, 6–Naphthyridines by Cyclization of 2–Styrylnicotinic Acid Amides," *Khimiya Geterotsik–licheskikh Soedinenii*, No. 6, 783–5 (1984).

Sigova, V.I. and Konshin, M.E., "Synthesis and Reactions of 8–Benzylidene–2–Methyl–5,6,7, 8–Tetrahydroquinoline–3–Carboxylic Acid Arylamides," *Khimiya Geterotsik–licheskikh Soedinenii*, No. 4, 506–8 (1986).

Ukhov, S.V. and Konshin, M.E., Naphthyridines: 2–Methylquinoline–3–Carboxanilides and the Synthesis Therefrom of 2–Substituted 1–OXO–3–Phenyl–1,2,3,4–Tetrahydrobenzo [b]–1,6–Naphthyridines, *Khimiya Geterotsik–licheskikh Soedinenii*, No. 2, 238–40 (1989).

Borer, B. et al., "The First Synthesis of the ABCD Ring System of Manzamine A. Construction of the Macrocyclic Ring D.," *Tetrahedron Letters*, vol. 35, No. 19, 3191–4 (1994).

Coste, J. et al., "BROP: A New Reagent for Coupling N–Methylated Amino Acids," *Tetrahedron Letters*, vol. 31, No. 5, 669–72 (1990).

Crimmins, M. and King, B., "An Effecient Asymmetric Approach to Carbocyclic Nucleosides: Asymmetric Synthesis of 1592U89, a Potent Inhibitor of HIV Reverse Transcriptase," *J. Org. Chem.*, vol. 61, 4192–3 (1996).

Crowe, W. and Zhang, Z., "Highly Selective Cross–Metathesis of Terminal Olefins," *J. Am. Chem. Soc.*, vol. 115, No. 23, 10998–9 (1993).

Fu, G. and Grubbs, R., "Synthesis of Cycloalkemes Via Alkylidene–Mediated Olefin Metathesis and Carbonyl Olefination," *J. Am. Chem. Soc.*, vol. 115, 3800–1 (1993).

Fu, G. and Grubbs, R., "Synthesis of Nitrogen Heterocycles Via Catalytic Ring–Closing Metathesi of Dienes," *J. Am. Chem. Soc.*, vol. 114, 7324–5 (1992).

Fu, G. and Grubbs, R., "The Application of Catalytic Ring–Closing Olefin Metathesis to the Synthesis of Unsaturated Oxygen Heterocycles," *J. Am. Chem. Soc.*, vol. 114, 5426–7 (1992).

Fu, G. et al., "Catalytic Ring–Closing Metathesis of Functionalized Dienes by a Ruthenium Carbene Complex," *J. Am. Chem. Soc.*, vol. 115, 9856–7 (1993).

Fujimura, O. and Grubbs, R., "Asymmetric Ring–Closing Metathesis: Kinetic Resolution Catalyzed by a Chiral Molybdenum Alkylidene Complex," *J. Am. Chem. Soc.*, vol. 118, 2499–2500 (1996).

Fujimura, O. et al., "The Synthesis of Cyclic Enol Ethers Via Molybdenum Alkylidene–Catalyzed Ring–Closing Metathesis," *Journal of Organic Chemistry*, vol. 59, No. 15, 4029–31 (1994).

Fürstner, A. and Langemann, K., "Conformationally Unbiased Macrocyclization Reactions by Ring Closing Metathesis," *J. Org. Chem.*, vol. 61, 3942–3 (1996).

Balkenhohl, F. et al., "Combinatorial Synthesis of Small Organic Molecules", *Angew. Chem. Int. Ed. Engl.*, 35:2288–2337 (1996).

Malardeau C. and Mousset G., "Isomèrisations en Sèie Dioxolanne–1,3. Synthése D'acètyl–3 Tètrahydrofurannes", Bulletin de la Sociètè Chimique de France, Part 2, No. 9–10, pp. 988–992, (Sep.–Oct. 1977).

* cited by examiner

RING OPENING METATHESIS OF ALKENES

This application is a division of U.S. patent application Ser. No. 08/818,197, filed Mar. 14, 1997, now U.S. Pat. No. 6,177,464, issued Jan. 23, 2001.

BACKGROUND OF THE INVENTION

The need for new classes of chemical compounds for use in pharmaceutical and agricultural applications has received much attention. For example, modern synthetic chemical methods for producing regio- and stereochemically defined compounds have made possible drugs with previously unattainable activity and specificity. Nevertheless, many currently-available drugs have been designed to avoid structural complexity, due to the traditionally difficult task of economically developing compounds with dense and diverse functional arrays. Thus, new methods for the production of functionally and stereochemically diverse compounds have the potential to exploit this heretofore underexplored area.

Transition-metal mediated olefin metathesis has been recognized as an effective means for carbon—carbon bond formation (see, e.g., Grubbs, R. H.; Miller, S. J.; Fu, G. C. Acc. Chem. Res. (1995) 28:446; Schmalz, H. -G. Angew. Chem. Int. Ed Engl. (1995) 34(17):1833). Ring closing-metathesis has been extensively utilized for the synthesis of macrocycles, carbocycles and heterocycles (see (a) Fu, G. C. Grubbs, R. H. J. Am. Chem. Soc. (1992) 114:5426. (b) Fu, G. C. Grubbs, R. H. J Am. Chem. Soc. (1992) 114:7324. (c) Fu, G. C.; Grubbs, R. H. J. Am. Chem. Soc. (1993) 115:3800. (d) Fu, G. C.; Nguyen, S. T.; Grubbs, R. H. J. Am. Chem. Soc. (1993) 115:9856. (e) Fujimura, O.; Fu. G. C.; Grubbs, R. H. J. Org. Chem. (1994) 59:4029. (f) Kim, S. -H.; Bowden, N.; Grubbs, R. H. J. Am. Chem. Soc. (1994) 116:10801. (g) Miller, S. J.; Kim, S. -H.; Chen, Z. -R; Grubbs, R. H. J. Am. Chem Soc. (1995) 117:2108. (h) Miller, S. J.; Grubbs, R. H. J. Am. Chem. Soc. (1995) 117:5855. (i) Martin, S. F.; Liao, Y.; Rein, T. Tetrahedron Lett. (1994) 35:691. (j) Borer, B. C.; Deerenberg, S.; Bieraugel, H.; Pandit, U. K. Tetrahedron Lett. (1994) 35:3191. (k) Martin, S. F.; Liao, Y.; Chen. H. J.; Patzel, M.; Ramser, M. N. Tetrahedron Lett. (1994) 35:6005. (l) Martin, S. F.; Wagman, A. S. Tetrahedron Lett. (1995) 36:1169. (m) Houri, A. F.; Xu, Z.; Cogan, D.; Hoveyda, A. J. Am. Chem. Soc. (1995) 117:2943. (n) Kim, S. -H.; Zuercher, W. J.; Bowden, N. B.; Grubbs, R. H. J. Org. Chem. (1996) 61:1073. (o) Fürstner, A.; Langemann, K. J. Org. Chem. (1996) 61:3942. (p) Crimmins, M. T.; King, B. W. J. Org. Chem. (1996) 61:4192. (q) Zuercher, W. J.; Hashimoto, M.; Grubbs, R. H. J. Am. Chem. Soc. (1996) 118:6634). However, the application of intermolecular ring opening cress-metathesis (ROM) for the convergent synthesis of small organic molecules has remained relatively unexplored. Recently, solution-phase ROM of fused and bicyclic olefin systems with aliphatic alkenes yielding cyclopentane and tetrahydrofuran derivatives was reported (see (a) Schneider, M. F.; Blechert, S. Angew. Chem. Int. Ed. Engl. (1996) 35: 411. (b) Randall, M. L.; Tallarico, J. A.; Snapper, M. L. J. Am. Chem. Soc. (1995) 117:9610. (c) Schneider, M. F.; Lucas, N.; Velder, J.; Blechert, S. Angew. Chem. Int. Ed. Engl. (1997) 36: 257). (d) Snapper et al. J. Am. Chem. Soc. 119:1478 (1997)). For unsymmetrically substituted substrates only slight regioselectivity was generally observed. In addition, other reaction pathways, such as ring opening metathesis polymerization of the bicyclic or fused olefins competed with the desired cross-metathesis reactions.

Terminal aryl olefins have been shown to participate in selective cross-metathesis reactions utilizing a molybdenum alkylidene catalyst (see Crowe, W. E.; Zhang, Z. J. J. Am. Chem. Soc. (1993) 115:10998). The cross-metathesis of norbornene and styrene in the presence of $Ru_2(OAc)_4$ and ethyldiazoacetate has also been reported (see Noels, A. F.; Demonceau, A.; Carlier, E.; Hubert A. J.; Márquez-Silva, R. -L.; Sánchez-Delgado, R. A. J. Chem. Soc., Chem. Commun. (1988) 783). However, an extensive utilization of aryl olefins in ROM has been absent.

Thus, previously reported ROM methods suffer from drawbacks which can render them undesirable for the synthesis of highly complex chemical compounds.

SUMMARY OF THE INVENTION

The invention relates to ring-opening cross-metathesis reactions, and to substituted cyclic compounds, libraries of compounds, and methods of preparing and using the compounds.

In one aspect, the invention provides a compound represented by the formula (Formula I):

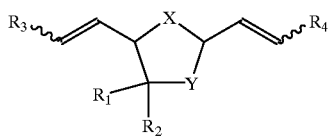

in which

X is a direct bond or a moiety selected from the group consisting of O, S, $NR_5$, and $CR'_1R'_2Q$;

Y is a moiety selected from the group consisting of O, S, $NR_5$, and $CR_1R_2Q$;

Q is independently for each occurrence a direct bond or a moiety selected from the group consisting of O, S, $NR_5$, and $CR_1R_2$;

$R_1$ and $R_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R'_1$ and $R'_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R_3$ and $R_4$ are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy;

$R_5$ is independently for each occurrence hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;

or a first occurrence of $R_1$ or $R_2$, taken together with a second occurrence of $R_1$ or $R_2$, and the carbon atoms to which they are attached, form a carbocyclic or heterocyclic ring;

or at least one of $R_1$, $R_2$, $R'_1$, $R'_2$, or $R_5$ is a linker group to a solid support;

or a salt thereof.

In another embodiment, the invention provides compounds represented by the formula (Formula Ia):

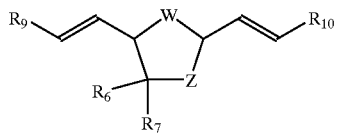

in which

W is $CH_2$ or O;

Z is $CHC(O)R_8$ or $NR_5$;

$R_5$ is hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;

$R_6$ and $R_7$ taken together are O, or $R_6$ is $CHC(O)R'_8$ and $R_7$ is hydrogen;

$R_8$ and $R'_8$ are each independently hydroxy, alkoxy, aryloxy, or amino; and one of $R_9$ and $R_{10}$ is hydrogen and the other of $R_9$ and $R_{10}$ is alkyl or aryl;

or a salt thereof.

In another aspect, the invention provides compounds represented by the formula (Formula II):

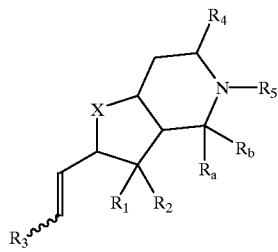

in which

X is a direct bond or a moiety selected from the group consisting of O, S, $NR_5$, and $CR'_1R'_2Q$;

Q is a direct bond or a moiety selected from the group consisting of O, S, $NR_5$, and $CR_1R_2$;

$R_1$ and $R_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R'_1$ and $R'_2$ are each independently hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R_3$ and $R_4$ are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy;

$R_5$ is independently for each occurrence hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;

$R_a$ and $R_b$ are each hydrogen, or $R_a$ and $R_b$ taken together are O;

or a salt thereof.

In another aspect, the invention provides a method for performing a ring opening cross-metathesis reaction on a solid support. The method includes the step of reacting an immobilized bicyclic alkene with an olefin under ring opening cross-metathesis conditions, such that ring opening cross-metathesis occurs on a solid support.

In another aspect, the invention provides methods of preparing a compound of Formula I. The method includes the step of reacting a bicyclic alkene represented by the formula (Formula III):

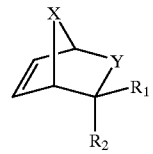

in which

X is a direct bond or a moiety selected from the group consisting of O, S, $NR_5$, and $CR'_1R'_2Q$;

Y is a moiety selected from the group consisting of O, S, $NR_5$, and $CR_1R_2Q$;

Q is independently for each occurrence a direct bond or a moiety selected from the group consisting of O, S, $NR_5$, and $CR_1R_2$;

$R_1$ and $R_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R'_1$ and $R'_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R_5$ is independently for each occurrence hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;

or a first occurrence of $R_1$ or $R_2$, taken together with a second occurrence of $R_1$ or $R_2$, and the carbon atoms to which they are attached, form a carbocyclic or heterocyclic ring;

or at least one of $R_1$, $R_2$, $R'_1$, $R'_2$, or $R_5$ is a linker group to a solid support;

or a salt thereof;

with a compound of the formula (Formula IV):

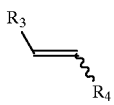

in which

R_3 and R_4 are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy; under ring opening cross-metathesis conditions, such that a compound of Formula I, Formula Ia, or Formula II is prepared.

In another aspect, the invention provides libraries of compounds of Formula I, Formula Ia or Formula II, and methods for preparing such libraries.

In another aspect, the invention provides pharmaceutical compositions. The pharmaceutical compositions include a compound of Formula I, Formula Ia or Formula II in a pharmaceutically acceptable vehicle.

In another aspect, the invention provides a method for treating a bacterial infection. The method includes the step of administering to a subject in need thereof an effective amount of a compound of Formula I or Formula Ia, such that the bacterial infection is treated.

DETAILED DESCRIPTION OF THE INVENTION

The invention relates to methods for performing ring opening cross-metathesis (ROM) reactions on solid supports, and to compounds and libraries of compounds prepared by such methods.

Applying solid-phase synthesis techniques to ROM can effectively isolate the olefin immobilized on the resin, preventing unwanted olefin polymerization (see Schuster, M.; Pernerstorfer, J.; Blechert, S. *Angew. Chem. Int. Ed. Engl.* (1996) 35: 1979). In addition, a solid-phase methodology can be conveniently incorporated into combinatorial library strategies (see, e.g., (a) DeWitt, S. H.; Czarnik, A. W. *Acc. Chem. Res.* (1996) 29:114. (b) Armstrong, R. W.; Combs, A. P.; Tempest, P. A.; Brown, S. D.; Keating, T. A. *Acc. Chem. Res.* (1996) 29:123. (c) Ellman, J. A. *Acc. Chem. Res.* (1996) 29:132. (d) Gordon, E. M.; Gallop, M. A.; Patel, D. V. *A.cc. Chem. Res.* (1996) 29:144. (e) Lowe, G. *Chem. Soc. Rev.* (1995) 309), for producing an array of highly functionalized molecular scaffolds, e.g., as described infra, preferably in a diastereospecific manner. For example, it has now been found that ROM reactions performed on a solid support can have a product distribution different from the corresponding ROM reaction performed in the solution phase. As described below, ROM on solid support can have significantly improved regioselectivity and/or stereoselectivity compared to solution-phase ROM. As described in more detail below, solid-phase ROM provides access to highly substituted and functionalized molecular scaffolds, e.g., cyclopentyl, fused cyclopentyl, and tetrahydrofuranyl and fused tetrahydrofuranyl molecular platforms in a regioselective and stereoselective fashion.

Definitions

The term "electron-releasing substituent" is known in the art (see, e.g., J. March, "Advanced Organic Chemistry", 3rd Edition, Wiley-InterScience (1991)), and, as used herein, refers to a substituent of an aryl group which has a greater tendency to release electron density to the aryl group than does a hydrogen atom. Exemplary electron releasing substituents include alkoxy (e.g., methoxy), substituted or unsubstituted amino (e.g., dimethylamino), alkylthio (e.g., methylthio), and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, cyclic anhydrides, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, aralkyl, or an aromatic or heteroaromatic moiety.

The term "stannyl," as used herein, refers to a group represented by the formula:

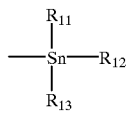

in which $R_{11}$ and $R_{12}$ and $R_{13}$ are each independently alkyl or aryl The term "silyl," as used herein, refers to a group represented by the formula:

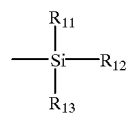

in which $R_{11}$, $R_{12}$ and $R_{13}$ are each independently alkyl or aryl.

The term "boronato," as used herein, refers to a group represented the formula:

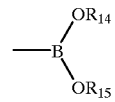

in which $R_{14}$ and $R_{15}$ are each independently alkyl, aryl, or a salt-forming cation.

The term "heteroatom" as used herein means an atom of any element other than carbon or hydrogen. Preferred heteroatoms are nitrogen, oxygen, sulfur and phosphorus.

The term "linker group," as used herein, refers to a linking or spacing moiety which can be used to covalently or non-covalently link a compound to a solid support. Linker groups suitable for use in the invention are known in the art for use in solid-phase synthesis.

The term "substantially pure," as used herein, refers to a compound which is substantially free of impurities, including (but not limited to) starting materials, side products, and the like. A compound is "substantially pure" if it comprises at least about 80%, more preferably 90%, still more preferably at least about 95% of the composition. If a single isomer of a compound is desired (e.g., a single diastereomer, enantiomer, or regioisomer), the compound is preferably substantially free of any undesired isomers (e.g., the unwanted enantiomer, diastereomers, or regioisomers), i.e., the desired isomer comprises at least about 80%, more preferably 90%, still more preferably at least about 95% of the weight of the isomers present in the composition.

The term "subject," as used herein, refers to an animal, more preferably a warm-blooded animal, most preferably a mammal, including cattle, sheep, pigs, horses, dogs, cats, rats, mice, and humans.

The term "treating a bacterial infection," as used herein, refers to preventing an infection, preventing spread of an infection, or decreasing the extent or severity of a bacterial infection. In a preferred embodiment, the bacterial infection is cured, i.e., substantially eliminated.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, alkenes can include either the E- or Z- geometry, where appropriate.

I. Compounds

In one aspect, the invention provides compounds which can be represented by the formula (Formula I):

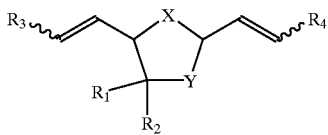

in which
- X is a direct bond or a moiety selected from the group consisting of O, S, $NR_5$, and $CR'_1R'_2Q$;
- Y is a moiety selected from the group consisting of O, S, $NR_5$, and $CR_1R_2Q$;
- Q is independently for each occurrence a direct bond or a moiety selected from the group consisting of O, S, $NR_5$, and $CR_1R_2$;
- $R_1$ and $R_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or R1 and R2 taken together are O or S;
- $R'_1$ and $R^1_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;
- $R_3$ and $R_4$ are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy, with the proviso that $R_3$ and $R_4$ are not both hydrogen;
- $R_5$ is independently for each occurrence hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;
- or a first occurrence of $R_1$ or $R_2$, taken together with a second occurrence of $R_1$ or $R_2$, and the carbon atoms to which they are attached, form a carbocyclic or heterocyclic ring;
- or at least one of $R_1$, $R_2$, $R'_1$, $R'_2$, or $R_5$ is a linker group to a solid support;
- or a salt thereof.

In certain preferred embodiments, at least one of $R_1$, $R_2$, $R'_1$, $R'_2$, or $R_5$ is a linker group to a solid support. In preferred embodiments, $R_3$ and $R_4$ are not the same, i.e., are different moieties. In preferred embodiments, at least one of $R_3$ and $R_4$ is aryl. In particularly preferred embodiments, $R_3$ and $R_4$ are not both hydrogen. In preferred embodiments, X is not a direct bond. In certain embodiments, X is O, while in other embodiments, X is $CH_2$. In certain preferred embodiments, Q is a direct bond. In preferred embodiments, $R_5$ is $-CH_2C(O)R_8$, in which $R_8$ is hydroxy, alkoxy, aryloxy, or amino.

In certain preferred embodiments, if X is $CH_2$ or O, and Y is methylene (i.e., Y is $CR_1R_2Q$ and Q is a direct bond), then $R_3$ and $R_4$ are different. In certain preferred embodiments, if X is $CH_2$ or O, and Y is methylene (i.e., Q is a direct bond), then $R_1$ and $R_2$ are different. In certain preferred embodiments, if X is a direct bond, and Y is $CR_1R_2Q$, then Q is not $CR_1R_2$. In preferred embodiments, if X is $CH_2$ or O, and Y is $NR_5$ or $CR_1R_2Q$, and Q is a direct bond, then at least one of $R_3$ and $R_4$ is aryl. In preferred embodiments, if X is O, and one of $R_3$ and $R_4$ is aryl, the other of $R_3$ and $R_4$ is not alkyl.

In particularly preferred embodiments, the compounds of the invention can be represented by the formula (Formula Ia):

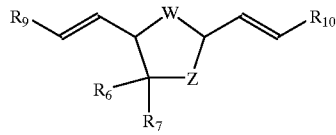

in which
- W is $CH_2$ or O;
- Z is $CHC(O)R_8$ or $NR_5$;
- $R_5$ is hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;
- $R_6$ and $R_7$ taken together are O, or $R_6$ is $CHC(O)R'_8$ and $R_7$ is hydrogen; and
- $R_8$ and $R'_8$ are each independently hydroxy, alkoxy, aryloxy, or amino;
- or a salt thereof.

In preferred embodiments of the compounds of Formula Ia, if Z is $NR_5$, then $R_6$ and $R_7$ taken together are O. In certain preferred embodiments, Z is $CHC(O)R_8$, $R_6$ is $CHC(O)R'_8$ and $R_7$ is hydrogen. In preferred embodiments, at least one of $R_5$, $R_8$ and $R'_8$ is a linker to a solid support. In certain preferred embodiments, one of $R_9$ and $R_{10}$ is an aryl group which is substituted with one or more electron-releasing substituents; more preferably, one of $R_9$ and $R_{10}$ is a 4-methoxyphenyl group. In preferred embodiments, W is $CH_2$. In certain preferred embodiments, Z is $CHC(O)R_8$, $R_6$ is $CHC(O)R'_8$ and $R_7$ is hydrogen.

Thus, the invention provides a wide variety of highly substituted and functionalized compounds, e.g., substituted cyclobutanes, oxetanes, β-lactams, cyclopentanes, cyclohexanes, tetrahydrofurans, tetrahydropyrans, pyrrolidines, piperidines, 2-oxapiperidines, 1,3-dioxanes, tetrahydrothiophenes, and the like. For example, when X and Y in the compound of Formula I are both carbon (and Q is a direct bond), the compound is a cyclopentane derivative. In another example, when X is a direct bond in the compound of Formula I, Y is carbon (and Q is a direct bond), the compound of Formula I is a cyclobutane derivative. In yet another example, when X is $NR_5$, and Y is carbon (and Q is a direct bond) the compound is a substituted pyrrolidine.

Compounds such as substituted cyclopentanes, tetrahydrofurans, and pyrrolidines are common in nature, and are also present in a variety of synthetic compounds including pharmaceuticals and agrochemicals. For example, prostaglandins and other prostanoids are substituted cyclopentane or cyclopentene derivatives. Muscarine, a naturally-occurring alkaloid, is a cholinomimetic which includes the tetrahydrofuran structure. Nicotine is a substituted pyrrolidine which has been used as an agricultural insecticide. The invention thus provides analogs or derivatives of these and other compounds, and methods of preparing such compounds, as described herein.

Moreover, the compounds of the invention can have a variety of closely spaced functionalities and may serve as interesting molecular scaffolds. Such molecular scaffolds can be used to present pharmacophores to certain receptors. For example, the compounds of the invention, having suitable functional groups, may have biological activity such as CNS activity, activity at steroid receptors, antiinflammatory activity, protein kinase C inhibitory activity, antifungal or antibacterial activity, opiate receptor activity, and the like. For example, as described in Example 6, infra, certain of the compounds of the invention exhibit moderate antibacterial activity in in vitro screening assays.

In another embodiment, the invention provides compounds of Formula II:

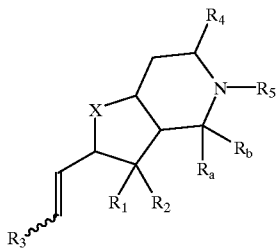

in which
  X is a direct bond or a moiety selected from the group consisting of O, S, $NR_5$, and $CR'_1R'_2Q$;
  Q is a direct bond or a moiety selected from the group consisting of O, S, $NR_5$, and $CR_1R_2$;
  $R_1$ and $R_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;
  $R'_1$ and $R'_2$ are each independently hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;
  $R_3$ and $R_4$ are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy;
  $R_5$ is independently for each occurrence hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;
  $R_a$ and $R_b$ are each hydrogen, or $R_a$ and $R_b$ taken together are O;
  or a salt thereof.

In preferred embodiments of the compound of Formula II, X is O or $CH_2$. In certain preferred embodiments of the compound of Formula II, $R_3$ is hydrogen. In certain preferred embodiments of the compound of Formula II, $R_4$ is aryl, and more preferably, aryl having at least one electron-releasing substituent. In certain preferred embodiments, $R_a$ and $R_b$ taken together are O. It will be appreciated by the skilled artisan that compounds in which $R_a$ and $R_b$ taken together are O can be converted to the corresponding compound in which $R_a$ and $R_b$ are each H by reduction, e.g., by treatment with diborane, as is known in the art.

In preferred embodiments, the compound of Formula I, Ia or II is substantially pure, i.e., the compound is at least 80%, 90% or 95% pure. Compounds which are not substantially pure can be purified by conventional methods, including the methods described infra.

It has now been found that the compounds of the invention have anti-bacterial activity. For example, as described in Example 6, infra, certain compounds of the invention have activity against gram-positive bacteria. Accordingly, in a preferred embodiment, a compound of the invention has anti-bacterial activity. Preferred compounds include compounds of Formula I in which X is $CH_2$. In certain preferred embodiments, $R_1$ is H. In some preferred embodiments, $R_3$ is H. In certain preferred embodiments, Y is carbon, e.g., —CH(C(O)$NR_9R_{10}$)—, in which $R_9$ and $R_{10}$ are each independently hydrogen or substituted or unsubstituted alkyl, alkenyl, alkynyl, aryl, cycloalkyl, or heterocyclyl; or $R_9$ and $R_{10}$, taken together with the nitrogen to which they are attached, form a heterocyclic ring.

II. Methods

In another aspect, the invention provides methods for performing ring-opening cross-metathesis reactions. In one embodiment, the method includes the steps of reacting an immobilized bicyclic alkene with a terminal olefin under ring opening cross-metathesis conditions, such that ring opening cross-metathesis occurs on a solid support. In a preferred embodiment, the terminal olefin is a terminal aryl olefin.

In another embodiment, the invention provides a method for performing ring opening cross-metathesis reactions of a bicyclic alkene with a terminal aryl olefin. The method includes the step of reacting a bicyclic alkene with a terminal aryl olefin under ring opening cross-metathesis conditions, such that ring opening cross-metathesis occurs.

The invention also provides a method for preparing a compound of Formula I. In one embodiment, the method includes the steps of reacting a compound represented by the formula (Formula III):

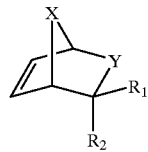

in which
  X is a direct bond or a moiety selected from the group consisting of O, S, $NR_5$, and $CR'_1R'_2Q$;
  Y is a moiety selected from the group consisting of O, S, $NR_5$, and $CR_1R_2Q$;
  Q is independently for each occurrence a direct bond or a moiety selected from the group consisting of O, S, $NR_5$, and $CR_1R_2$;
  $R_1$ and $R_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R'_1$ and $R'_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R_5$ is independently for each occurrence hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;

or a first occurrence of $R_1$ or $R_2$, taken together with a second occurrence of $R_1$ or $R_2$, and the carbon atoms to which they are attached, form a carbocyclic or heterocyclic ring;

or at least one of $R_1$, $R_2$, $R'_1$, $R'_2$, or $R_5$ is a linker group to a solid support;

or a salt thereof;

with a compound of the formula (Formula IV):

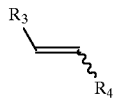

in which $R_3$ and $R_4$ are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy;

under ring opening cross-metathesis conditions, such that a compound of Formula I is prepared.

In preferred embodiments of the compound of Formula III, at least one of $R_1$, $R_2$, $R'_1$, $R'_2$, or $R_5$ is a linker group for covalently linking the compound of Formula I and/or Formula II to a solid support. Exemplary linker groups are described infra. In certain preferred embodiments, X is O or $CR'_1R'_2$. In certain preferred embodiments, if Y is $NR_5$, then $R_1$ and $R_2$ taken together are O.

In certain preferred embodiments of Formula III, in at least one occurrence $R_5$ is —C(O)$NR_{14}R_{15}$, in which $R_{14}$ and $R_{15}$ are each independently hydrogen or substituted or unsubstituted alkyl, alkenyl, alkynyl, aryl, cycloalkyl, or heterocyclyl; or $R_{14}$ and $R_{15}$, taken together with the nitrogen to which they are attached, form a heterocyclic ring. In preferred embodiments, one of $R_{14}$ and $R_{15}$ is hydrogen, i.e., $R_1$ is a monosubstituted carboxamide. In this embodiment, $R_1$ can comprise a linking moiety. In other embodiments, $R_{14}$ and $R_{15}$, taken together with the nitrogen to which they are attached, form a 1,4-piperazinyl moiety, which, in certain embodiments, can be substituted, e.g., with a linker moiety.

In preferred embodiments of the compound of Formula IV (hereinafter referred to as an "olefin"), if $R_4$ is aryl, then $R_3$ is hydrogen. In particularly preferred embodiments, $R_4$ is substituted aryl, in which the aryl group has at least one electron-releasing group.

In certain embodiments, the methods of the invention include the further step of purifying the compound of Formula I and/or Formula II (e.g., by washing the solid support upon which the compound is immobilized). In certain embodiments, the method includes the further step of cleaving the compound of Formula I and/or Formula II from the solid support. In certain embodiments, the method includes the step of purifying the compound (or compounds) produced in the ring opening cross-metathesis reactions. In certain embodiments, the compound or compounds of Formula I and/or Formula II can be further reacted, e.g., to produce derivatives and analogs of compounds of Formula I and/or Formula II.

The invention also provides methods for preparing a compound of Formula II. The method includes the steps of reacting a compound represented by the formula (Formula V):

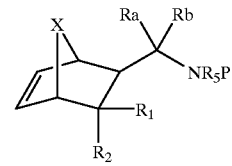

in which

X is a direct bond or a moiety selected from the group consisting of O, S, $NR_5$, and $CR'_1R'_2Q$;

Q is a direct bond or a moiety selected from the group consisting of O, S, $NR_5$, and $CR_1R_2$;

P is hydrogen or a protecting group;

$R_1$ and $R_2$ are each independently for each occurrence hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R'_1$ and $R'_2$ are each independently hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or $R_1$ and $R_2$ taken together are O or S;

$R_5$ is independently for each occurrence hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;

$R_a$ and $R_b$ are each hydrogen, or $R_a$ and $R_b$ taken together are O;

or a salt thereof;

with a compound represented by the formula (Formula IV):

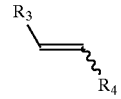

in which $R_3$ and $R_4$ are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy;

under ring opening cross-metathesis conditions, such that a cross-metathesis product is prepared; and cyclizing the cross-metathesis product, such that a compound of Formula II is prepared.

In preferred embodiments, the step of cyclizing the cross-metathesis product includes exposing the cross-metathesis product to acidic conditions, such that ring closure occurs. In preferred embodiments, the step of cyclizing the cross-metathesis product is performed without purification of the cross-metathesis product. In preferred embodiments, P is hydrogen or a protecting group which can be removed under the conditions of the step of cyclizing the cross-metathesis product, e.g., P can be removed under acidic conditions. Amine protecting groups which can be removed under acidic conditions are well known (e.g., the t-butyloxycarbonyl (BOC) group). For a discussion of suitable protecting groups, see, e.g., Greene and Wuts, "Protective Groups in Organic Synthesis," 2nd ed., Wiley, 1991). In the compounds of Formula V, the protecting group P can also be a solid support or a linker to a solid support (see, e.g., Examples 5 and 6, infra, in which cleavage from the solid support occurs under acidic conditions, with concomitant cyclization to compounds of Formula II).

The invention also provides methods for preparing compounds of Formula Ia. In one embodiment, the method includes the steps of reacting a compound represented by the formula (Formula VI):

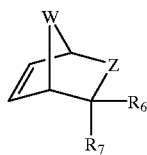

in which
  W is $CH_2$ or O;
  Z is $CHC(O)R_8$ or $NR_5$;
  $R_5$ is hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;
  $R_6$ and $R_7$ taken together are O, or $R_6$ is $CHC(O)R'_8$ and $R_7$ is hydrogen;
  $R_8$ and $R'_8$ are each independently hydroxy, alkoxy, aryloxy, or amino; and
  one of $R_9$ and $R_{10}$ is hydrogen and the other of $R_9$ and $R_{10}$ is alkyl or aryl;
  or a salt thereof;
with a compound represented by the formula (Formula VII)

under ring opening cross-metathesis conditions, such that a compound of Formula Ia is prepared. In preferred embodiments, the bicyclic alkene is immobilized on a solid support. In particularly preferred embodiments, the ring opening cross-metathesis reaction is a regioselective reaction.

In preferred embodiments of the methods of the invention, the ring-opening cross-metathesis conditions include a catalyst, preferably a molybdenum or ruthenium catalyst, such as are described herein.

The methods of the invention provide several advantages over ring opening cross-metathesis reactions previously reported. For example, when the bicyclic alkene of Formula III is immobilized on a solid support, the undesired polymerization of the bicyclic alkene, which may be a significant side reaction when ROM reactions are performed in the solution phase, can be minimized. Furthermore, the ROM reactions of the invention proceed cleanly, in good yield, and are the products can be easily and quickly isolated and purified, often by simply filtering the solid support, washing to remove impurities, and cleaving the product from the solid support.

The present method can also provide stereo- and regioselective ROM reactions. For example, as described in Example 3, infra, the ROM reactions of the invention can be more regioselective than the corresponding ROM performed in the solution-phase. Thus, higher yields of a desired product can be obtained, with less wasted side product (e.g., undesired stereo- or regioisomers), thereby providing a more economical synthesis. Moreover, by appropriate choice of the substitutents of the bicyclic alkene and the olefin, the product ratio of the ROM reaction can be influenced to produce either one of two products in preference to the other. Thus, in a preferred embodiment, the ROM reactions of the invention are regioselective, i.e., produce one product in preference to a regioisomer of that product. In preferred embodiments, the mole ratio of regioisomers is at least about 1.5:1, more preferably at least about 2:1, and still more preferably at least about 3:1.

Similarly, judicious selection of substituents can provide compounds having pre-selected stereochemistry. For example, the rigid bicyclic framework of a bicyclic alkene can be chosen such that the ring-opened product bears an array of functional groups in predictable stereochemical relation. For example, when a compound of Formula III is employed in the methods of the invention, the resulting cyclic compound of Formula I will have an $R_2$ substituent (if any) on the ring which is cis relative to the vinyl groups bearing $R_3$ and $R_4$. Moreover, the use of chiral reactants or chiral solid supports can promote the predominant formation of one enantiomer of two possible enantiomeric products.

Reactants

In general, the solid-phase ROM reactions of the invention involve reaction of a bicyclic alkene with an olefin. In certain embodiments, bicyclic alkenes which can be used in the methods of the invention can be represented by Formula III, Formula V, or Formula VI. A variety of bicyclic alkenes having the general structure of Formula III, Formula V, or Formula VI are known in the art, and many bicyclic alkenes can be purchased commercially.

Bicyclic alkenes suitable for use in the methods of the invention will be sufficiently reactive to undergo a ROM reaction with an alkene (usually in the presence of a catalyst). Without wishing to be bound by theory, it is believed that ring strain increases the rate of ROM reaction of a bicyclic alkene, i.e., relief of ring strain provides a driving force for ROM. Accordingly, highly strained bicyclic alkenes are preferred. Bicyclic alkenes contemplated for use in the methods of the invention include compounds having a [2.2.1], [2.2.2] or [3.2.0] ring system. Bicyclic alkenes having a [2.2.1] ring system are preferred. Illustrative examples of bicyclic alkenes include substituted or unsubstituted compounds norbornene, norbornadiene, 7-oxanorbornene, 7-oxanorbornadiene, and the like.

In preferred embodiments, the bicyclic alkene of Formula III, Formula V, or Formula VI is immobilized on a solid support. Such immobilization can be covalent, or can be due to ionic, hydrophobic, hydrophilic, or other interactions between the compound and the support. Linkers can be used to provide for convenient attachment to, and release from, the solid support (see infra). Thus, the bicyclic alkene preferably includes at least one functional group which can be used to immobilize the bicyclic alkene on the solid support.

An olefin which reacts with a bicyclic alkene in a ROM reaction preferably has the structure shown in Formula IV. In preferred embodiments, if either of $R_3$ and $R_4$ is aryl, the olefin is monosubstituted (i.e., the remaining substituents of the olefinic bond are hydrogen). Thus, terminal aryl olfins are preferred for reaction with a bicyclic alkene. If neither of $R_3$ and $R_4$ is aryl, the olefin can be a 1,2-disubstituted olefin (having either the E- or Z-configuration at the double bond). In certain embodiments, at least one of $R_3$ and $R_4$ can comprise a functional group (e.g., a linker moiety) which can be used to immobilize the olefin on a slid support.

It has been found that terminal aryl olefins having at least one electron-releasing substituent can react to provide products with high regioselectivity (See, e.g., Example 3, infra). Accordingly, in certain embodiments, terminal aryl olefins having at least one electron-releasing substituent are preferred. However, in certain embodiments, the use of an aryl olefin having an electron-releasing substituent can result in the undesired regioisomeric product; accordingly, in certain embodiments, the aryl group does not include an electron-releasing substituent. The skilled artisan will be able to select appropriate substituents of the olefin (e.g., substituted aryl groups) for a particular product using no more than routine experimentation.

Catalysts

Catalysts useful in the methods of the invention include catalysts known in the art to be useful for ring opening or ring-closing cross-metathesis or polymerization reactions. Examples of such catalysts include the catalysts described in U.S. Pat. No. 5,342,909 and 4,945,144, both to Grubbs et al. Other catalysts may find use in the methods of the invention. In general, such catalyst are alkylidene complexes of transition metals such as molybdenum or ruthenium. For examples of catalysts useful in olefin metathesis reactions, see, e.g., thee references cited in notes 2 and 8, infra. A catalyst will generally be selected to have suitable activity with a selected bicyclic alkene and olefin. For example, certain catalysts can be sensitive to particular functional groups of the bicyclic alkene or olefin, which can deactivate a catalyst. In such a case, another catalyst should be chosen. In light of the teachings herein, the choice of an appropriate catalyst can be made by the skilled artisan using no more than routine experimentation.

In certain embodiments, the catalyst can be prepared in an immobilized form (i.e., immobilized on an inert solid support) for ease of handling and recycling (see, e.g, Nyugen et al, *J. Orgmet. Chem.* 497:195–200 (1995)).

Linkers

Linkers useful for immobilizing compounds on a solid support are well known in the art and include, e.g., diamino linkers, phenylene moieties, and the like. A particularly preferred linker is the linker described in Hauske, J. R.; Dorff, P. *Tetrahedron Lett.* 1995, 36, 1589. This linker is easily synthesized, stable under a variety of reaction conditions, and readily cleaved to release the product from the solid support.

It will be understood that the linker can be selected to have a length which permits facile reaction with a substrate compound immobilized on a solid support. For example, the linker should be long enough to avoid steric encumbrance of the immobilized compound by the solid support. The linker can be selected to be cleavable under a variety of conditions (e.g., hydrolytic, nucleophilic, electrolytic, oxidative, photolytic, and the like), if desired, as is known in the art. The skilled artisan will appreciate that the choice of linker, in combination with the choice of solid support, can influence factors such as reaction time, completeness of reaction, releasability of the reaction products, and the like. Thus, the linker and solid support will in general be selected to permit ready immobilization, reaction, isolation, and purification of the compounds of the invention.

Solid supports

Solid supports suitable for use in solid phase synthesis are known in the art (for examples, see, e.g., M. Bodansky "Principles of Peptide Synthesis", 2nd edition, Springer-Verlag, Berlin (1993); Hauske, J. R.; Dorff, P. *Tetrahedron Lett.* 1995, 36, 1589; and references cited therein). Many such art-recognized solid supports are useful in the methods of the invention. For example, solid supports suitable for use in the present invention include suitably modified forms of: silica (e.g., particles such as silica gel), silicon (e.g., wafers or chips), glass (e.g., a glass plate or controlled pore glass beads), polystyrene, polyacrylamide, Tenta-Gel, Wang resin, Rapp resin, Merrifield resin, Rink resin, and the like.

Reaction Conditions

The reactions of the present invention may be performed under a wide range of conditions, though it will be understood that the solvents and temperature ranges recited herein are not limitative and only correspond to a preferred mode of the process of the invention.

In general, it is desirable that reactions are run using mild conditions that will not adversely affect the bicyclic alkene, the olefin, the catalyst, the intermediates, the resin, the linker or the products. For example, the reaction temperature influences the speed of the reaction, as well as the stability of the reactants, resin, and catalyst. The reactions will usually be run at temperatures in the range of −78° C. to 100° C., more preferably in the range −20° C. to 50° C. and still more preferably in the range −20° C. to 25° C.

In general, the reactions according to the invention will be performed in a liquid medium, e.g., in a suspension of a solid support in a liquid medium. The reactions may be run in an inert solvent, preferably one in which the reaction ingredients, optionally including the polymeric support, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. The reactions can be conducted under anhydrous conditions and in certain embodiments it is preferable to perform the reactions under an inert atmosphere of a gas such as nitrogen or argon.

The progress of the metathesis reactions can be monitored by techniques known to one of ordinary skill in the art. For example, aliquots of the reaction mixture can be taken at intervals and the aliquots tested, e.g., by cleavage of compounds from the solid support followed by spectroscopic analysis of the crude reaction mixture. Alternatively, the reaction can be monitored by chromatographic techniques such as thin-layer chromatography (TLC) or HPLC.

In certain embodiments, the methods for preparing compounds include the further step of purifying the compounds. Purity of the reaction products can be determined according to known techniques. If the products are impure, they can be purified according to a variety of methods known in the art. For example, compounds immobilized on a solid support can be separated from some impurities by simple filtration and washing of the solid support to remove soluble impurities. Compounds which are not immobilized on solid supports can be purified by methods including crystallization (where the compound is crystalline), trituration, distillation, and chromatographic techniques such as TLC and HPLC (analytical or preparative scale), flash chromatography, and the like. The selection of methods for purifying compounds will be routine for the ordinarily skilled artisan.

In preferred embodiments, the purity of a compound produced according to the methods of the invention is at least about 50%, more preferably at least about 70%, still more preferably at least about 90%, and most preferably at least about 95%.

In another aspect, the invention provides methods for treating bacterial infection. In general, the method comprises administering to a subject in need thereof an effective amount of a compound of the invention, such that the bacterial infection is treated. The compound of the invention can be, e.g., a compound of Formula I or Formula II, and can optionally be administered in a pharmaceutically acceptable vehicle. Bacterial infections which can be treated according to the methods of the invention include (but are not limited to) infections due to gram-positive bacteria such as *Staphylococcus aureus*, methicillin-resistant *S. aureus* (MRSA), or vancomycin-resistant *Enterococcus faceium* (VREF). It will be understood that more than one compound of the invention can be employed to treat a bacterial infection; such multi-drug therapy can be useful to provide a broader spectrum of action against bacteria or to prevent the development of drug-resistant bacterial strains.

As is described in more detail below, a compound of the invention can be administered to a subject topically, e.g., to treat a localized bacterial infection, or systemically, e.g., to treat a systemic bacterial infection. The compound of the invention is preferably administered such that the bacterial infection is cured.

In certain preferred embodiments, the compound is a compound of Formula I in which X is $CH_2$. In certain preferred embodiments, $R_1$ is H. In some preferred embodiments, $R_3$ is H. In certain preferred embodiments, Y is carbon, e.g., —$CH(C(O)NR'_{14}R'_{15})$—, in which $R'_{14}$ and $R'^1_5$ are each independently hydrogen or substituted or unsubstituted alkyl, alkenyl, alkynyl, aryl, cycloalkyl, or heterocyclyl; or $R'_{14}$ and $R'_{15}$, taken together with the nitrogen to which they are attached, form a heterocyclic ring.

III. Libraries

In another aspect, the invention provides libraries of compounds of Formula I, Formula Ia or Formula II, and methods of preparing such libraries.

The synthesis of combinatorial libraries is well known in the art and has been reviewed (see, e.g., E. M. Gordon et al., *J. Med. Chem.* 37:1385–1401 (1994)). Thus, the subject invention contemplates methods for synthesis of combinatorial libraries of compounds of Formula I or Formula II. Such libraries can be synthesized according to a variety of methods. For example, a "split-pool" strategy can be implemented in the following way: beads of a functionalized polymeric support are placed in a plurality of reaction vessels. To each aliquot of beads is added a solution of a different bicyclic alkene, and the reactions proceed to yield a plurality of immobilized bicyclic alkenes. The aliquots of derivatized beads are then washed, "pooled" (i.e., recombined), and the pool of beads is again divided, with each aliquot being placed in a separate reaction vessel. To each reaction vessel is added a solution of a different olefin in solution (e.g., a terminal aryl olefin) and a catalyst, and reaction occurs to yield a plurality of reaction vessels each containing a plurality of compounds of Formula I immobilized on solid support. The library of immobilized compounds can then be washed to remove impurities. In certain embodiments, the compound of Formula I can further be treated (e.g., by cleavage, if desired, and cyclization) to yield a compound of Formula II.

In another illustrative method of combinatorial synthesis, a "diversomer library" is created by the method of Hobbs, DeWitt et al. (*Proc. Natl. Acad. Sci. U.S.A.* 90:6909 (1993)). Aliquots of functionalized polymeric support beads are placed in an array of reaction vessels, and one of a plurality of bicyclic alkenes is introduced into each vessel. After reaction, the beads are washed to yield an array of immobilized bicyclic alkenes. Each vessel in the array is then reacted with one of a plurality of olefins, in the presence of a catalyst. After reaction, purification and workup yields a soluble library of substituted compounds of Formula I and/or Formula II.

Other synthesis methods, including the "tea-bag" technique of Houghten (see, e.g., Houghten et al., *Nature* 354:84–86 (1991)) can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J Med. Chem.*, op. cit.). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are known in the art (see, e.g., E. M. Gordon et al., *J. Med. Chem.* 37:1385–1401 (1994)).

Combinatorial libraries of compounds can also be synthesized with "tags" to encode the identity of each member of the library (see, e.g., W. C. Still et al., U.S. Pat. No. 5,565,324 and PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In preferred embodiments, the libraries of compounds of the invention contain at least 30 compounds, more preferably at least 100 compounds, and still more preferably at least 500 compounds. In preferred embodiments, the libraries of compounds of the invention contain fewer than $10^9$ compounds, more preferably fewer than $10^8$ compounds, and still more preferably fewer than $10^7$ compounds.

A library of compounds is preferably substantially pure, i.e., substantially free of compounds other than the intended products, e.g., members of the library. In preferred embodiments, the purity of a library produced according to the methods of the invention is at least about 50%, more preferably at least about 70%, still more preferably at least about 90%, and most preferably at least about 95%.

The libraries of the invention can be prepared according to the methods of the invention, wherein at least one of the bicyclic alkene and the olefin is provided as a variegated population. In a preferred embodiment, the methods for preparing libraries are performed on a solid support (i.e., at least one of the bicyclic alkene or the olefin is immobilized on a solid support). The term "variegated population", as used herein, refers to a population including at least two different chemical entities, e.g., of different chemical structure. For example, a "variegated population" of bicyclic alkenes would comprise at least two different bicyclic alkenes. Similarly, a variegated population of olefins comprises at least two different olefins. Use of a variegated population of linkers can produce a variety of compounds upon cleavage of the linkers (see, e.g., Example 6, infra). Thus, the methods of the invention also can include the further step of providing a variegated population of linkers.

Libraries of the invention are useful, e.g., for drug discovery. For example, a library of the invention can be screened (e.g., according to the methods described herein) to determine whether the library includes compounds having a pre-selected activity. Thus, for example, a library can be screened to determine whether compounds of the library have anti-bacterial activity or any other activity which can be detected in vitro or in vivo, e.g., anti-inflammatory activity, enzyme inhibitory activity, and the like.

IV Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect by treating (i.e., preventing or ameliorating) a bacterial infection in a subject, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds can contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, a any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the peptidomimetic in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral or topical administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the derivative (e.g., ester, salt or amide) thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient, when used for the indicated effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Exemplification

General Experimental

Nuclear magnetic resonance (NMR) spectra were recorded using a 300 MHz Varian Unity Fourier transform NMR spectrometer. Low resolution mass spectra (LRMS) were obtained by direct injection of samples in methanol into a single quadrapole mass spectrometer (Finnigan SSQ 7000) equipped with an atmospheric pressure ionization module (APCI-MS). High resolution mass spectroscopy (HRMS) was performed by M-Scan, West Chester, Pa. Elemental analyses were performed by Atlantic Microlabs, Inc., Norcross, Ga. High pressure liquid chromatography (HPLC) was performed on a Hewlett-Packard 1090 instrument with a $C_{18}$ column (4.6 mm×25 cm) and a diode array detector (peakwidth: 0.53 min, sampling interval: 0.32 min, spectrum from 200–350 nm). A flow rate of 1 mL/min, oven temperature of 40° C. and an injector volume of 4 μL were used. The eluent was a mixture of water and acentonitrile both containing 0.05% trifluoroacetic acid (TFA). HPLC samples were prepared in water/acetonitrile (1:1). A small amount of methanol was sometimes added to increase solubility. The following two methods were used:

| Gradient time table: | | |
|---|---|---|
| Time (min) | % Water | % Acetonitile |
| Method A: Run time: 15 min | | |
| 0 | 95 | 5 |
| 4 | 60 | 40 |
| 8 | 0 | 100 |
| 11 | 0 | 100 |
| 12 | 95 | 5 |
| 15 | 95 | 5 |
| Method B: Run time: 18 min | | |
| 0 | 50 | 50 |
| 5 | 35 | 65 |
| 9 | 15 | 85 |
| 11 | 10 | 90 |
| 12 | 5 | 95 |
| 14 | 5 | 95 |
| 15 | 50 | 50 |
| 18 | 50 | 50 |

All metathesis reactions were conducted under an argon atmosphere in dichloromethane (Aldrich Chem. Co.) stored under nitrogen in SurelSeal™ bottles. All reagents obtained from commercial sources were used without further purification, unless otherwise indicated. Bis(tricyclohexylphosphine)benzylidine ruthenium dichloride, 1, was purchased from Strem Chemicals, Inc. Wang Resin (1% divinylbenzene cross-linked; 0.85–1.01 mmol/g; 100–200 mesh) was purchased from Advanced ChemTech, Louisville, Ky. The resin was saturated with reaction solvent prior to use. For metathesis reactions the resin was saturated with dichloromethane in an inert atmosphere prior to the addition of the other reaction materials.

EXAMPLE 1

In order to assess the potential structure diversity that could result from ROM, we chose to evaluate aryl olefin substrates first in solution-phase reactions. For the metathesis reactions described in this example, the commercially available $(Cy_3P)_2Cl_2Ru=CHPh$, 1, was used. In the presence of a terminal aryl olefin substrate cross-metathesis can occur generating a different ruthenium phenylalkylidene catalyst. However, Grubbs recently communicated that the electronic effect of the phenylalkylidene moiety of 1 on metathesis activity was relatively small (see (a) Schwab, P.; Grubbs, R. H.; Ziller, J. W. *J Am. Chem. Soc.* (1996) 118:100. (b) Schab, P.; France M. B.; Ziller, J. W.; Grubbs, R. H. *Angew. Chem. Int. Ed. Engl.* (1995) 34, 2039).

When bicyclic olefin 2 (0.12M in dichloromethane) was allowed to react at room temperature with 4-vinylanisole (5 eq.) in the presence of 1 (5 mol %) tetrasubstituted cyclopentane 3 was produced in 61% isolated yield (Scheme 1).

Scheme 1

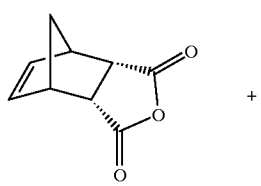

+

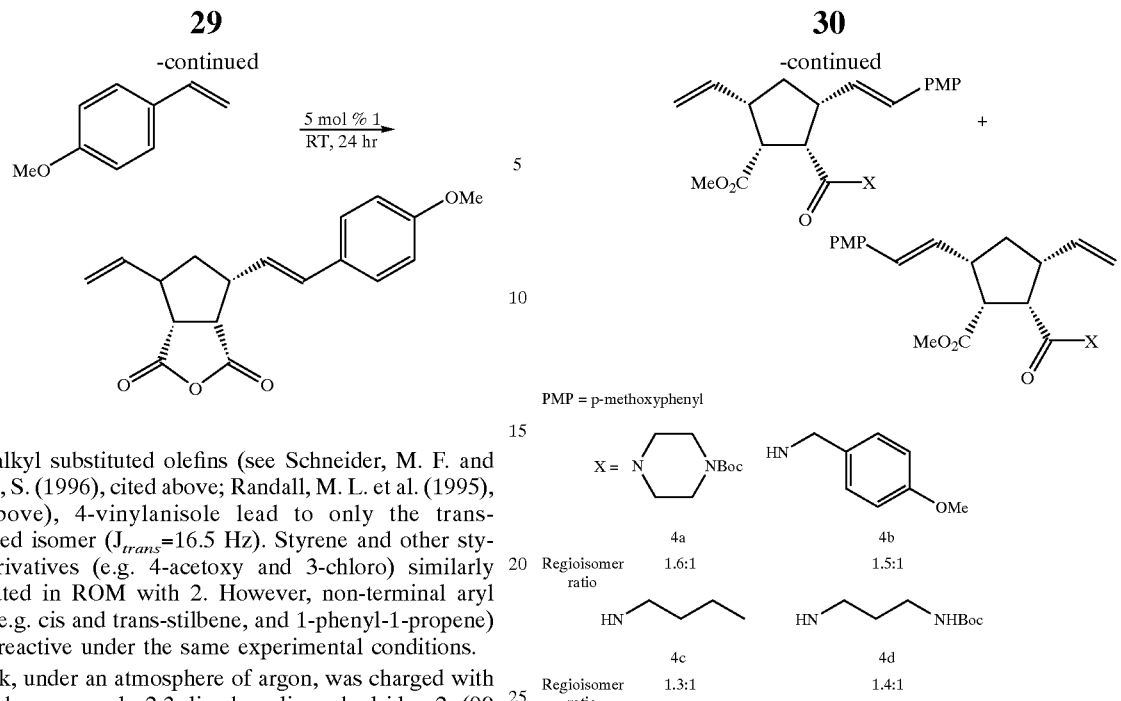

PMP = p-methoxyphenyl $X =$

| 4a | 4b |
|---|---|
| Regioisomer ratio 1.6:1 | 1.5:1 |
| 4c | 4d |
| Regioisomer ratio 1.3:1 | 1.4:1 |

Unlike alkyl substituted olefins (see Schneider, M. F. and Blechert, S. (1996), cited above; Randall, M. L. et al. (1995), cited above), 4-vinylanisole lead to only the trans-substituted isomer ($J_{trans}$=16.5 Hz). Styrene and other styrene derivatives (e.g. 4-acetoxy and 3-chloro) similarly participated in ROM with 2. However, non-terminal aryl olefins (e.g. cis and trans-stilbene, and 1-phenyl-1-propene) were unreactive under the same experimental conditions.

3: A flask, under an atmosphere of argon, was charged with cis-5-norbomene-endo-2,3-dicarboxylic anhydride, 2 (90 mg, 0.548 mmol), dichloromethane (4.5 mL), 4-vinylanisole (364 μL, 2.74 mmol), and 1 (23 mg, 5 mol %). The reaction mixture was allowed to stir at room temperature for 24 h. The mixture was concentrated. The residue was dissolved in ethyl acetate/hexane (50:50) and passed through a small plug of silica gel. Decolorizing carbon was added to the solution before it was filtered. The filtrate was concentrated and the residue purified by column chromatogaphy on silica gel using hexane/ethyl acetate (75:25) as the eluent to give 99 mg (61% yield) of 3 as a white crystalline solid. $^1$H NMR (300 MHz, $CD_2Cl_2$): δ 1.54 (q, 1H, J=12.9 Hz); 2.10 (m, 1H); 3.00–3.20 (m, 2H); 3.50–3.59 (m, 2H); 3.79 (s, 3H); 5.18 (pent, 1H, J=1.2 Hz); 5.20–5.32 (m, 1H); 5.97 (sept, 1H, $J_1$,=7.5 Hz, $J_2$=3.0 Hz); 6.13 (dd, 1H, $J_1$,–15.8 Hz, $J_2$=7.8 Hz); 6.47 (d, 1H, J=15.8 Hz); 6.86 (d, 2H, J=8.6 Hz); 7.32 (d, 2H, J=8.6 Hz); $^{13}$C{$^1$H} NMR (75 MHz, $CD_2Cl_2$): δ 37.11, 46.69, 47.21, 50.06, 50.53, 55.78, 114.5, 117.29, 125.00, 128.01, 130.06, 131.80, 135.83, 159.91, 171.39, 171.46; Elemental Analysis: (cal.) C 72.47, H 6.08; (found) C 72.40, H 6.12.

EXAMPLE 2

Several unsymmetrically substituted bicyclic olefins (4a–d) were allowed to react with 4-vinylanisole utilizing solution-phase ROM conditions. Slow addition of the bicyclic olefin (via a syringe pump) minimized undesired polymerization (see Schneider, M. F. and Blechert, S. (1996), cited above; Randall, M. L. et al. (1995), cited above). However, in all cases two isomers were produced with only slight regioselectivity (Scheme 2).

Scheme 2

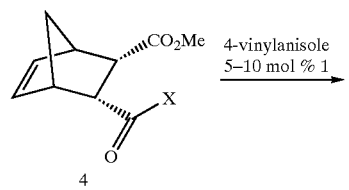

4-vinylanisole
5–10 mol % 1

Preparation of 4a:
Resin 8 (900 mg, 0.675 mmol; prewashed with dichloromethane) was treated with 10 mL 50% TFA in dichloromethane for 20 min. The resin was washed with dichloromethane (4×10 mL). The eluents were combined and then concentrated. The residue was redissolved in dimethylformamide (DMF) (5 mL) and then triethylamine (1.0 mL) was added followed by di-tert-butyldicarbonate (162 mg, 0.743 mmol). The reaction mixture was stirred at room temperature overnight. The mixture was diluted with water (50 mL) and extracted with ethyl acetate (2×50 mL). The organic extracts were combined, washed sequentially with water (50 mL) and brine (50 mL), dried over anhydrous magnesium sulfate, filtered, and concentrated to give a yellow oil. The oil was purified by column chromatography on silica gel using hexane/ethyl acetate (1:1) as eluent to give 4a (190 mg). $^1$H NMR (300 MHz, $CDCl_3$): δ 1.20–1.48 (m, 1 1H); 3.10–3.70 (m, 12H); 6.16 (dd, 1H, $J_1$=5.6 Hz, $J_2$=3.0 Hz); 6.41 (dd, 1H, $J_1$=5.6 Hz, $J_2$=3.0 Hz); $^{13}$C{$^1$H} NMR (75 MHz, $CDCl_3$): δ 28.56, 41.83, 45.27, 47.01, 47.08, 47.13, 48.62, 49.04, 51.79, 80.20, 80.38, 133.52, 136.55, 154.86, 171.15, 172.85.

Preparation of 4b:
A flask was charged with mono-methyl cis-5-norbornene-endo-2,3-dicarboxylate, 4e (500 mg, 2.55 mmol), dichloromethane (35 mL), 4-methoxybenzylamine (302 μL, 2.31 mmol), 1-hydroxybenzotriazole (HOBt) (338 mg, 2.50 mmol), and dicyclohexylcarbodiimide (DCC) (516 mg, 2.50 mmol). The reaction mixture was allowed to stir at room temperature for 24 h. The mixture was filtered. The filtrate was diluted with dichloromethane (20 mL) and then washed sequentially with saturated sodium bicarbonate (20 mL) and brine (20 mL), dried over anhydrous magnesium sulfate, filtered, and concentrated to give a white solid. The solid was recrystallized from 50% aqueous ethanol to give 4b as a white solid (473 mg). $^1$H NMR (300 MHz, $CD_2Cl_2$): δ 1.31 (d, 1H, J=8.3 Hz); 1.43 (d, 1H, J=8.3 Hz); 3.07 (s, 2H); 3.20 (s, 2H); 3.46 (s, 3H); 3.77 (s, 3H); 4.24 (m, 2H); 5.81 (bs, 1H); 6.07 (dd, 1H, $J_1$=5.4 Hz, $J_2$=3.0 Hz); 6.39 (dd, 1H, $J_1$,=5.4 Hz, $J_2$=3.0 Hz); 6.85 (d, 2H, J=8.6 Hz); 7.18 (d, 2H, J=8.6 Hz).

Preparation of 4c:

A flask was charged with mono-methyl cis-5-norbornene-endo-2,3-dicarboxylate, 4e (500 mg, 2.55 mmol), dichloromethane (35 mL), n-butylamine (228 μL, 2.31 mmol), HOBt (338 mg, 2.50 mmol), and DCC (516 mg, 2.50 mmol). The reaction mixture was allowed to stir at room temperature for 24 h. The mixture was filtered. The filtrate was diluted with dichloromethane (20 mL) and then washed sequentially with saturated sodium bicarbonate (20 mL) and brine (20 mL), dried over anhydrous magnesium sulfate, filtered, and concentrated to give a white solid. The solid was purified by column chromatography on silica gel using hexane/ethyl acetate (1:1) as eluent to give 4c as a white solid. The sample was contaminated with 5% benzotriazole. $^1$H NMR (300 MHz, CDCl$_3$): δ 0.91 (t, 3H, J=7.1 Hz); 1.30–1.50 (m, 6H); 3.10–3.24 (m, 6H); 3.60 (s, 3H); 5.45 (bs, 1H); 6.16 (dd, 1H, $J_1$,=5.6 Hz, $J_2$=3.0 Hz); 6.50 (dd, 1H, $J1$,=5.6 Hz, $J_2$=3.0 Hz).

Preparation of 4d:

Resin 7 (400 mg, 0.340 mmol; prewashed with dichloromethane) was treated with 5 mL 50% TFA in dichloromethane for 30 min. The resin was washed with dichloromethane (4×5 mL). The eluents were combined and then concentrated. The residue was redissolved in dichloromethane (5 mL) and then triethylamine (1.0 mL) was added followed by di-tert-butyldicarbonate (164 mg, 0.75 mmol). The reaction mixture was stirred at room temperature for 2 h. The mixture was diluted with water (25 mL) and extracted with dichloromethane (3×25 mL). The organic extracts were combined, washed with brine (25 mL), dried over anhydrous magnesium sulfate, filtered, and concentrated (bath temperature<30° C.) to give a white oily solid. The residue was purified by column chromatography on silica gel using hexane/ethyl acetate (20:80) as eluent to give 4d (69 mg). $^1$H NMR (300 MHz, CDCl$_3$): δ 1.32–1.48 (m, 11H); 3.09–3.30 (m, 10); 3.58 (s, 3H); 5.13 (bs, 1H); 6.15 (dd, 1H, $J_1$=5.5 Hz, $J_2$=3.0 Hz); 6.46 (dd, 1H, $J_1$,=5.5 Hz, $J_2$=3.0 Hz).

ROM of 4a:

A flask, under an atmosphere of argon, was charged with 1 (7 mg, 6 mol %), dichloromethane. (3 mL), and 4-vinylanisole (92 μL, 5 eq). A solution of 4a (50 mg, 0.138 mmol) in dichloromethane (6 mL) was added over a 6 h period by syringe pump. The resulting reaction mixture was allowed to stir at room temperature overnight. The mixture was concentrated. The residue was purified by column chromatogaphy on silica gel using hexane/ethyl acetate (60:40) as the eluent to a colorless oil (42 mg).

ROM of 4b:

A flask, under an atmosphere of argon, was charged with 1 (7 mg, 6 mol %), dichloromethane (4 mL), and 4-vinylanisole (92 μL, 5 eq). A solution of 4b (34.8 mg, 0.110 mmol) in dichloromethane (5 mL) was added over a 12 h period by syringe pump. The resulting reaction mixture was allowed to stir at room temperature for an additional 8 h. The mixture was concentrated. The residue was purified by column chromatogaphy on silica gel using a gradient of hexane/ethyl acetate (75:25 to 60:40) as the eluent to a white semi-solid (43 mg).

ROM of 4c:

A flask, under an atmosphere of argon, was charged with 1 (3.5 mg, 6 mol %), dichloromethane (2 mL), and 4-vinylanisole (46 μL, 5 eq). A solution of 4c (17.3 mg, 0.069 mmol) in dichloromethane (3 mL) was added over a 6 h period by syringe pump. The resulting reaction mixture was allowed to stir at room temperature for an additional 18 h. The mixture was concentrated. The residue was purified by column chromatogaphy on silica gel using hexane/ethyl acetate (75:25) as the eluent to an oil (23 mg).

ROM of 4d:

A flask, under an atmosphere of argon, was charged with 1 (3.5 mg, 8.7 mol %), dichloromethane (2 mL), and 4-vinylanisole (46 μL, 8.2 eq). A solution of 4d (18.7 mg, 0.053 mmol) in dichloromethane (3 mL) was added over a 6 h period by syringe pump. The resulting reaction mixture was allowed to stir at room temperature for an additional 9 h. The mixture was concentrated. The residue was purified by column chromatogaphy on silica gel using hexane/ethyl acetate (50:50) as the eluent to an oil (16 mg). Regioisomer ratio determined by $^1$H NMR.

EXAMPLE 3

In order to evaluate solid-phase ROM, a bicyclic olefin substrate was attached to Wang resin, 5 (0.85–1.01 mmol/g). First, 5 was allowed to react with 1,1'-carbonyldiimidizole (CDI) followed by treatment with 1,3-propanediamine to give 6 (Scheme 3) (see, e.g., Hauske, J.R; Dorff, P. *Tetrahedron Lett.* (1995) 36:1589). The resin was acylated with bicyclic olefin 4e in the presence of PyBOP (PyBOP: benztriazole-1-yl-oxy-tris-pyrrolidinophosphonium hexafluorophosphate. Coste, J.; Dufour, M. -N.; Pantaloni, A.; Castro, B. *Tetrahedron Lett.* (1990) 31, 669) and N-methylmorpholine (NMM) to give 7. Similarly, resin 8 was prepared utilizing the same protocol, except piperazine was substituted for 1,3-propanediamine.

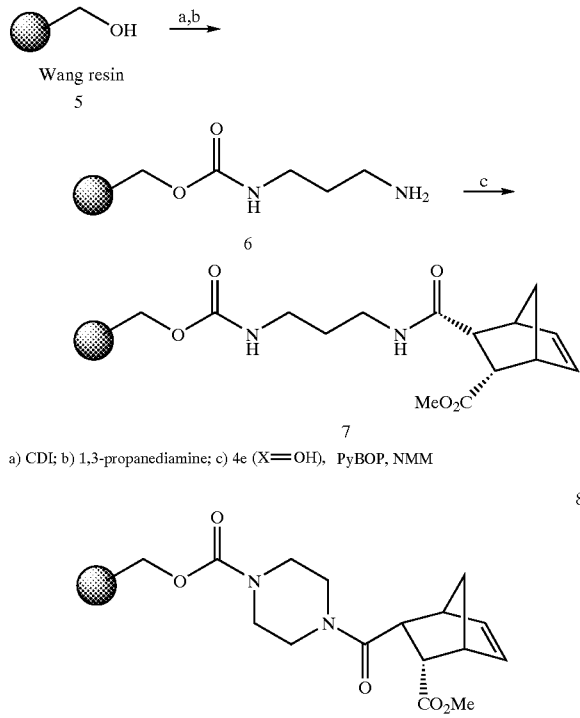

Resin 7 was allowed to react with 3-chlorostyrene (10 eq.) in the presence of 1 (10 mol %) at room temperature for 8 h. After sequential washing with DMF, methanol and dichloromethane, the resin was treated with 50% trifluoroacetic acid (TFA) in dichloromethane for 30 min yielding a mixture of regioisomer products 9a and 9b in a ratio of 1:1 (regioisomer ratios were determined either by $^1$H NMR analysis of the crude reaction material or by HPLC analysis of the corresponding t-butylcarbamate derivatives, which gave better separation). Likewise, resin 8 was allowed to react with 4-vinylanisole, followed by TFA treatment, to give a mixture of 10a and 10b in a ratio of 2.7:1. The overall isolated yield (based on resin loading) of the highly functionalized cyclopentane products was 60–70%. The solid-phase ROM reaction was compatible with an array of electronically differentiated terminal aryl olefins including 4-acetoxystyrene, 4-trifluoromethylstyrene, and 3-nitrostyrene.

Resin 5a:

Wang Resin 5 (4.5 g, 3.8 mmol; prewashed with THF) was shaken with CDI (3.1 g) in THF (50 mL) at room temperature for overnight. The resin was washed sequentially with THF (50 mL), DMF (2×50 mL), MeOH (2×50 mL), and dichloromethane (2×100 mL). The resin was dried under vacuum.

Resin 7:

Resin 5a (2.0 g, 1.7 mmol); prewashed with THF) was shaken with 1,3-propanediamine (708 μL) in THF (20 mL) at room temperature for 3 h. The resin was washed sequentially with THF (20 mL), MeOH (2×20 mL), and dichloromethane (2×50 mL) to give resin 6. Resin 6 was prewashed with DMF before being shaken with mono-methyl cis-5-norbornene-endo-2,3-dicarboxylate, 4e (1.33 g), PyBOP (3.78 g), and NMM (1.6 mL) in DMF for 3 h. The resin was washed sequentially with THF (2×20 mL), MeOH (2×20 mL), and dichloromethane (2×20 mL). The resin was dried under vacuum. A sample was cleaved from the resin with 50% TFA in dichloromethane and analyzed by HPLC.

Resin 8:

Resin 5a (2.0 g, 1.7 mmol); prewashed with THF) was shaken with piperazine (0.731 g) in THF (20 mL) at room temperature for 3 h. The resin was washed sequentially with THF (20 mL), MeOH (2×20 mL), and dichloromethane (2×50 mL). The resin was prewashed with DMF before being shaken with mono-methyl cis-5-norbornene-endo-2, 3-dicarboxylate, 4e (1.33 g), PyBOP (3.78 g), and NMM (1.6 mL) in DMF for 3 h. The resin was washed sequentially with THF (2×20 mL), MeOH (2×20 mL), and dichloromethane (2×20 mL). The resin was dried under vacuum. A sample was cleaved from the resin with 50% TFA in dichloromethane and analyzed by HPLC.

ROM of 7:

A reaction tube, under an atmosphere of argon, was charged with resin 7 (100 mg, 0.085 mmol) (Scheme 4). The resin was washed with dichloromethane. The tube was then charged with dichloromethane (1.0 mL), 3-chlorostyrene (108 μl, 0.85 mmol), and 1 (7 mg, 10 mol %). The tube was sealed under an atmosphere of argon and shaken at room temperature for 20 h. The resin was washed sequentially with DMF (3 mL), MeOH (2×3 mL), and dichloromethane (5×3 mL). The resin was treated with 50% TFA in dichloromethane (1.5 mL) for 30 min. The resin was washed with dichloromethane (5×3 mL). The washings were concentrated to 9a/9b as an oil.

The oil, 9a/9b, was dissolved in dichloromethane (2 mL) and then treated with triethylamine (250 μL) and d-tert-butyldicarbonate (41 mg) for 4 h. A sample of BOC-(N-butyloxycarbonyl) protected 9a/9b was analyzed by HPLC.

The oil, 10a/10b, was dissolved in dichloromethane (2 mL) and then treated with triethylamine (250 μL) and di-tert-butyldicarbonate (41 mg) for 4 h. A sample of BOC-protected 10a/10b was analyzed by HPLC.

ROM of 8:

A reaction tube, under an atmosphere of argon, was charged with resin 8 (100 mg, 0.085 mmol). The resin was washed with dichloromethane. The tube was then charged with dichloromethane (1.0 mL), 4-vinylanisole (113 μl, 0.85 mmol), and 1 (7 mg, 10 mol %). The tube was sealed under an atmosphere of argon and shaken at room temperature for 20 h. The resin was washed sequentially with DMF (3 mL), MeOH (2×3 mL), and dichloromethane (5×3 mL). The resin was treated with 50% TFA in dichloromethane (1.5 mL) for 30 min. The resin was washed with dichloromethane (5×3 mL). The washings were concentrated to 10a/10b as an oil. After lyophilization the overall yield was 68.3%. HRMS: (cal) 399.2283, (found) 399.2279.

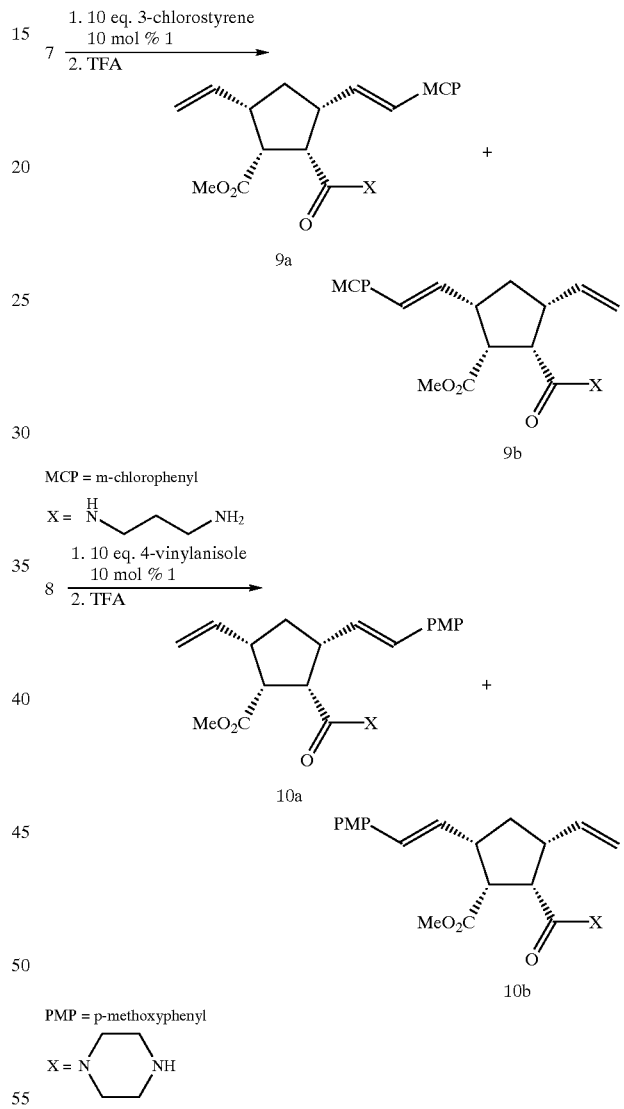

Scheme 4

EXAMPLE 4

The ability of bicyclic lactams to undergo ROM was examined as follows (Scheme 5):

Resin 11:

Resin 5a (100 mg. 0.085 mmol; prewashed with THF) was shaken with piperazine (37 mg) in THF (1 mL) at room temperature for 3 h. The resin was washed sequentially with THF (3 mL), MeOH (2×3 mL), and dichloromethane (3×3 mL). The resin was prewashed with DMF before being shaken with bromoacetic acid (118 mg) and DIC (54 μL).

The amide coupling was repeated. Then the resin was washed sequentially with DMF (3 mL), MeOH (2×3 mL), and dichloromethane (3×3 mL). The resin was shaken with potassium hydroxide (96 mg, finely powdered) and 2-azabicyclo[2.2.1]hept-5-en-3-one (46 mg) in dimethylsulfoxide (1 mL) at room temperature for 5 h. Then the resin was washed sequentially with water (5×3 mL), MeOH (3×3 mL), and dichloromethane (5×3 mL) and dried.

ROM of 11:

A reaction tube, under an atmosphere of argon, was charged with resin 11 (50 mg, 0.042 mmol). The resin was washed with dichloromethane. The tube was charged with dichloromethane (1.5 mL), 4-vinylanisole (57 μL), and 1 (8 mg). The tube was sealed under an atmosphere of argon and shaken at room temperature for 18 h. The resin was washed sequentially with DMF (3 mL), MeOH (2×3 mL), and dichloromethane (3×3 mL). The resin was treated with 50% TFA in dichloromethane (1 mL) for 30 min. The resin was washed with dichloromethane (3×3 mL). The washings were concentrated to give 12 as a mixture of regioisomers.

Scheme 5

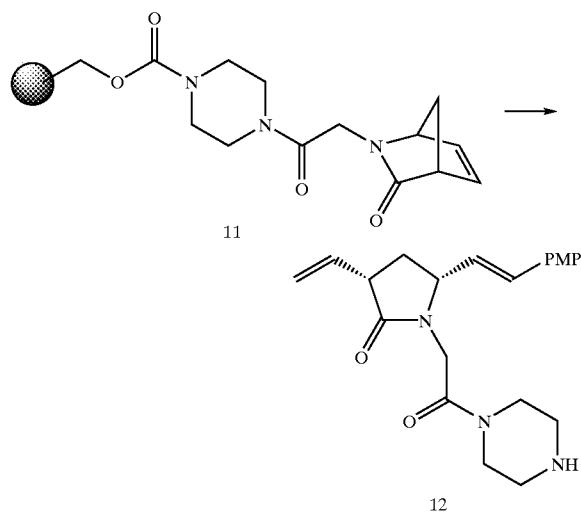

EXAMPLE 5

The ROM reactions of the invention also provide substituted tetrahydrofurans. Resin 6 was shaken with exo-3,6-epoxy-1,2,3,6-tetrahydrophthalic anhydride, followed by amidation of the free carboxylate with butylamine with PyBOP and NMM, to provide the resin 13 (Scheme 6). Reaction of resin 13 with 4-vinylanisole in the presence of 1, followed by TFA cleavage from the resin, provided the isomeric substituted tetrahydrofurans 14a and 14b as a mixture of regioisoomers in 70% yield.

Scheme 6

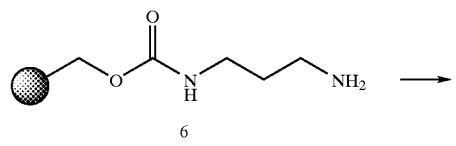

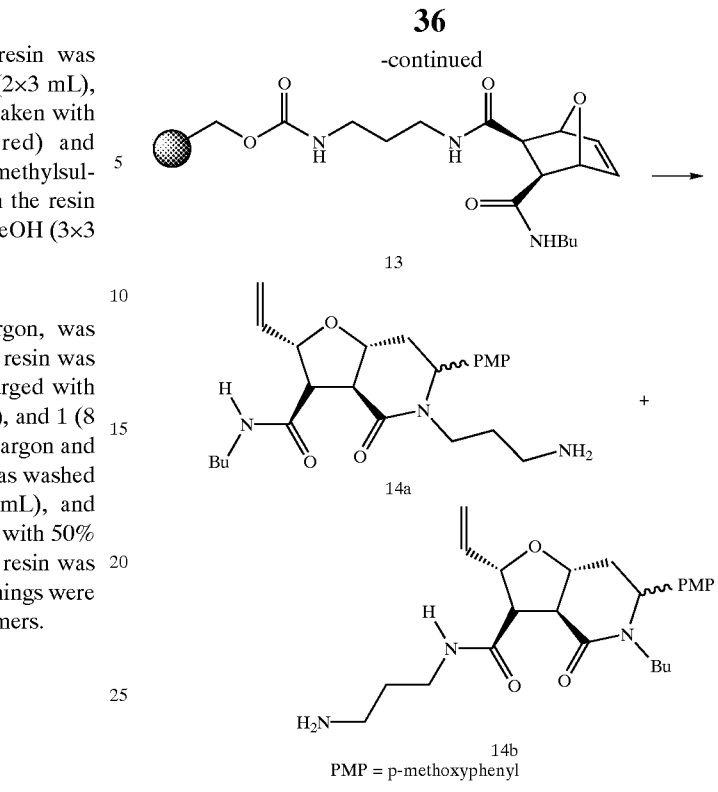

EXAMPLE 6

When resin 7 was allowed to react with 4-vinylanisole in the presence of 1, followed by treatment with 50% TFA in CDCl₃ only one major ROM product was produced in 77% overall yield (Scheme 7). Structure elucidation of the product by NMR revealed the fused bicyclic lactam 16. (For examples of similar cyclizations see, e.g.,: (a) Ukhov, S. V.; Konshin, M. E. *Khim. Geterosikl. Soedin.* 1992, 28, 92. (b) ) Ukhov, S. V.; Konshin, M. E. *Khim. Geterosikl. Soedin.* 1989, 25, 196. (c) Sigova, V. I.; Konshin, M. E. *Khim. Geterosikl. Soedin.* 1986, 22, 415. (d) Sigova, V. I.; Konshin, M. E. *Khim. Geterosikl. Soedin.* 1984, 20, 635. (e) Sigova, V. I.; Konshin, M. E. *Khim. Geterosikl. Soedin.* 1984, 22, 415. (f) Sigova, V. I.; Konshin, M. E. *Zh. Obshch. Khim.* 1984, 54, 1859.) Note that the solid-supported reaction provides greater regioselectivity than the solution-phase reaction The initial product of the cross-metathesis reaction evidently cyclizes under the acidic conditions employed.

Preparation of 16:

A reaction tube, under an atmosphere of argon, was charged with resin 7 (150 mg, 0.128 mmol). The resin was washed with dichloromethane. The tube was then charged with dichloromethane (1.5 mL), 4-vinylanisole (170 μl, 1.28 mmol), and 1 (11 mg, 10 mol %). The tube was sealed under an atmosphere of argon and shaken at room temperature for 20 h. The resin was washed sequentially with DMF (3 mL), MeOH (2×3 ml,), and dichloromethane (5×3 mL). The resin was treated with 50% TFA in CDCl₃ (1.5 mL) for 45 min. NMR analyses were performed (vida infra). After concentration and lyophilization the overall yield was 77%. $^1$H-NMR (300 MHz, CDCl₃/TFA) δ 7.40 (d, J=8.7 Hz, 2H); 7.08 (d, J=9 Hz, 2H); 5.83 (m, 1H); 5.18 (m, 2H); 4.61(dd, J=11.7, 3 Hz, 1H); 3.98 (s, 3H); 3.77(s, 3H); $^{13}$C NMR(300 MHz, CDCl₃/TFA) δ 178.39, 176.95, 159.79, 135.56, 130.73, 130.29, 117.24, 115.57, 64.25, 56.14, 53.19, 52.92, 47.12, 46.75, 42.73, 38.52, 37.25, 36.97, 34.19, 26.33.

Scheme 7

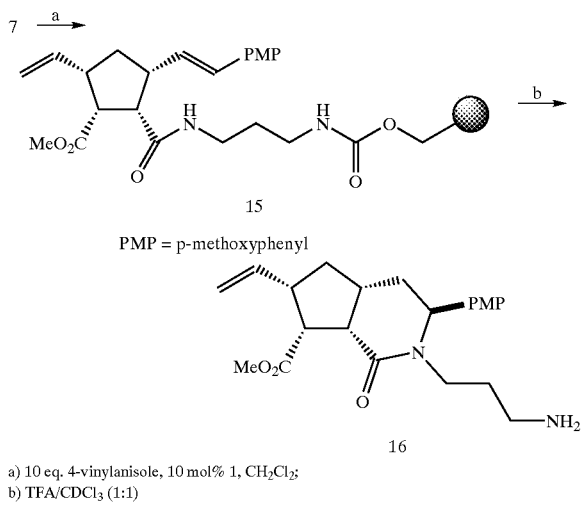

a) 10 eq. 4-vinylanisole, 10 mol% 1, CH$_2$Cl$_2$;
b) TFA/CDCl$_3$ (1:1)

EXAMPLE 7

A combinatorial library of compounds is prepared as follows:

Wang resin is treated with carbonyldiimidazole and then reacted, in 12 different reaction vessels, with 12 diamine compounds. The resulting amino-functionalized Wang resins are combined in groups of three to provide 4 reaction vessels, each containing 3 diamine-functionalized resins. To each reaction vessel is added bicyclic alkene 4e in the presence of PyBOP and NMM to provide bicyclic alkene immobilized to a solid support through a variety of linkers, and the four resin aliquots are further divided into eight reaction vessels each (for a total of 32 reaction vessels). Each vessels is treated with one of eight styrene derivatives in the presence of catalyst 1, and, after reaction is complete, the methyl ester of the bicyclic alkene is hydrolyzed to the carboxylic acid. The aliquots are divided into 24 vessels each (a total of 768 aliquots). Each vessel is treated with one of twenty-four different amines in the presence of PyBOP and NMM to provide 768 groups of compounds, each group containing compounds immobilized through one of three linkers. Where the ROM reaction is less than completely regioselective, two products can result; thus, a total of 4608 compounds (768×3×2) can be produced.

EXAMPLE 8

Two compounds were assayed for antibacterial activity in an in vitro assay system:

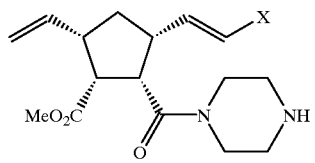

17: X=p-methoxyphenyl
18: X=n-butyl

Compounds 17 and 18 were synthesized as described above, cleaved from the solid support, and used as a mixture of regioisomers. Each test compound was then applied to a small disc of filter paper. The filter paper was placed in a petri dish in which *S. aureus*, methicillin-resistant *S. aureus* (MRS A), or vancomycin-resistant *E. faceium* (VREF) was inoculated. The bacterial cultures were incubated and then surveyed to determine the zone of inhibition (if any) of bacterial growth around each filter paper disc.

In each assay, both compound 17 and compound 18 displayed modest inhibitory activity against at least one organism.

Those skilled in the art will recognize, or be able to ascertain using no more than routine experimentation, numerous equivalents to the specific procedures described herein. Such equivalents are considered to be within the scope of this invention and are covered by the following claims.

The contents of all publications cited herein are hereby incorporated by reference.

Other embodiments are within the following claims.

What is claimed is:

1. A compound represented by the formula (Formula II):

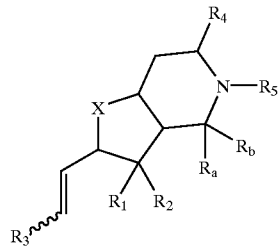

in which
X is CR'$_1$R'$_2$Q;
Q is a direct bond:
R$_1$ and R$_2$ are each independently hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or R$_1$ and R$_2$ taken together are O or S;
R'$_1$ and R'$_2$ are each independently hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or R'$_1$ and R'$_2$ taken together are O or S;
R$_3$ and R$_4$ are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy;
R$_5$ is hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;
R$_a$ and R$_b$ are each hydrogen, or R$_a$ and R$_b$ taken together are O;
or a salt thereof.

2. A method for preparing a compound represented by the formula (Formula II):

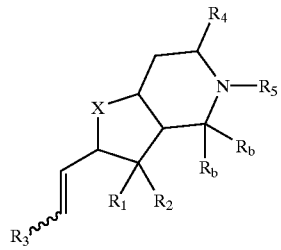

in which
- X is CR'$_1$R'$_2$Q;
- Q is a direct bond;
- R$_1$ and R$_2$ are each independently hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or R$_1$ and R$_2$ taken together are O or S;
- R'$_1$ and R'$_2$ are each independently hydrogen, halogen, or substituted or unsubstituted alkyl, alkenyl, alkynyl, aryl, heterocyclyl, amino, acylamino, hydroxy, alkoxy, aryloxy, carboxy, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio; or R'$_1$ and R'$_2$ taken together are O or S;
- R$_3$ and R$_4$ are each independently hydrogen, halogen, cyano, nitro, boronato, stannyl, silyl, or substituted or unsubstituted alkyl, alkenyl, alkynyl, aryl, cycloalkyl, heterocyclyl, carboxy, alkylcarbonyl, arylcarbonyl, alkoxycarbonyl, aryloxycarbonyl, aminocarbonyl, alkylcarbonyloxy, arylcarbonyloxy, or aminocarbonyloxy;
- R$_5$ is hydrogen or substituted or unsubstituted alkyl, alkenyl, alkynyl, aryl, alkylcarbonyl, arylcarbonyl, alkoxycarbonyl, aryloxycarbonyl, aminocarbonyl or heterocyclyl;
- R$_a$ and R$_b$ are each hydrogen, or R$_a$ and R$_b$ taken together are O;
- or a salt thereof;

the method comprising the steps of:

reacting a compound represented by the formula (Formula V):

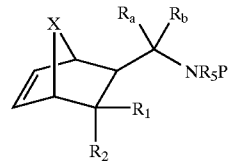

in which
- X, R$_1$, R$_2$, R$_5$, R$_a$ and R$_b$ are as defined above;
- and P is hydrogen or a protecting group;

with a compound represented by the formula (Formula IV):

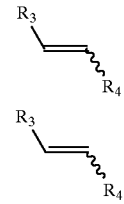

in which
- R$_3$ and R$_4$ are as defined above;
- under ring opening cross-metathesis conditions, such that a cross-metathesis product is prepared; and
- cyclizing the cross-metathesis product, such that a compound of Formula II is prepared.

3. The method of claim 2, in which the bicyclic alkene is immobilized on a solid support wherein R$_1$, R$_2$, R'$_1$, R'$_2$, or R$_5$ comprises a link to said solid support.

4. The method of claim 2, in which the ring opening cross-metathesis reaction is a regioselective reaction.

5. The method of claim 2, in which the step of cyclizing the cross-metathesis product includes exposing the cross-metathesis product to acidic conditions, such that ring closure occurs.

* * * * *